United States Patent
Chen

(10) Patent No.: US 9,853,675 B1
(45) Date of Patent: Dec. 26, 2017

(54) MULTISENSORY PHONE CASE

(71) Applicant: Ying Hai Chen, La Puente, CA (US)

(72) Inventor: Ying Hai Chen, La Puente, CA (US)

( * ) Notice: Subject to any disclaimer, the term of this patent is extended or adjusted under 35 U.S.C. 154(b) by 0 days.

(21) Appl. No.: 15/351,029

(22) Filed: Nov. 14, 2016

(51) Int. Cl.
  H04M 1/00 (2006.01)
  H04B 1/3888 (2015.01)
  G08B 7/06 (2006.01)

(52) U.S. Cl.
  CPC ............. H04B 1/3888 (2013.01); G08B 7/06 (2013.01)

(58) Field of Classification Search
  CPC .... H04B 1/3888; H04M 1/0202; H04M 1/185
  See application file for complete search history.

(56) References Cited

U.S. PATENT DOCUMENTS

| | | | | |
|---|---|---|---|---|
| 4,060,252 | A * | 11/1977 | Mowery | B65D 19/42 16/18 R |
| 7,551,899 | B1 * | 6/2009 | Nicolas | H04M 1/274558 379/355.01 |
| 2009/0082061 | A1 * | 3/2009 | Roh | H04M 1/72563 455/556.1 |
| 2009/0322498 | A1 * | 12/2009 | Yun | G06F 3/016 340/407.2 |
| 2015/0103018 | A1 * | 4/2015 | Kamin-Lyndgaard | G09G 5/006 345/173 |
| 2015/0215728 | A1 * | 7/2015 | Wilson | H04M 1/026 455/41.2 |
| 2015/0311941 | A1 * | 10/2015 | Sorrentino | H04M 1/185 455/575.8 |
| 2016/0142093 | A1 * | 5/2016 | Phang | H04B 1/3888 455/575.8 |
| 2016/0191680 | A1 * | 6/2016 | Jung | H04M 1/0241 455/575.1 |
| 2017/0091514 | A1 * | 3/2017 | Kang | G06K 9/00013 |

* cited by examiner

*Primary Examiner* — Tuan Pham
(74) *Attorney, Agent, or Firm* — WHGC, P.L.C.; John F. O'Rourke

(57) ABSTRACT

A mobile phone cover having a phone back, phone front, and a manipulable objects affixed to the phone back. The manipulable objects are configured to provide a user with sensory feedback that is tactile, visual, or audible or a combination of two or of three. A first tactile feedback includes a depress/release button and a corresponding audible feedback is a clicking sound. A second tactile feedback is rotary turning-in-place, and a corresponding audible feedback is a clicking sound or no sound. A third tactile feedback is a rocker motion and a corresponding audible feedback is a snapping sound. A fourth tactile feedback is an omnidirectional rolling ball and a corresponding audible feedback is no sound. A fifth tactile feedback is turnable gears and the corresponding audible feedback is a snapping sound. A sixth tactile feedback is depress/release half-domes and the corresponding audible feedback is a popping sound.

1 Claim, 2 Drawing Sheets

MULTISENSORY PHONE CASE

BACKGROUND OF THE INVENTION

1. Field of the Invention

The invention relates generally to mobile phone cases, and particularly, to mobile phone cases bearing sensory-motor feedback objects.

2. Background

Small manipulable objects with sensory appeal can be used as self-regulation tools to help with focus, attention, calming, and active listening. Some of these manipulable tools are called "fidgets." Although the vast majority of fidgets (hereinafter, "manipulable objects") are directed to children, particularly those with attention and learning difficulties, it has been observed that adults, too, may benefit from manipulable objects to help ameliorate anxiety, stress, and boredom. It also has been observed that many adults are equipped with a mobile phone, handling it frequently.

SUMMARY

Embodiments herein provide a mobile phone cover, including a hard yet resilient mobile phone back, configurable to attach to a mobile phone, and a manipulable object affixed to the back. The manipulable object is configured to provide a user with sensory feedback that is, without limitation, visual feedback, or tactile feedback, or audible feedback, or a combination of two or of three sensory feedback modes, when the manipulable object is manipulated. Embodiments also include a mobile phone front that can be coupleable to the mobile phone back. A perimeter of the mobile phone front can include a raised, pliable edge. The raised, pliable edge may have rectilinear shapes or curvilinear shapes, or a combination thereon. In an embodiment of the mobile phone cover back, the manipulable object makes a clicking sound when manipulated. In another embodiment, the manipulable object makes a popping sound when manipulated. In still another embodiment, the manipulable object makes a snapping sound when manipulated. In yet another embodiment, the manipulable object makes no sound when manipulated.

The manipulable object may take many forms. The manipulable object can be a captured disc which returns to shape, after being depressed/deflected. The manipulable object can be a captured disc which turns in a circle parallel to the mobile phone back. The manipulable object can be a captured rocker switch-like object which rocks back and forth. The manipulable object can be a captured ball bearing-like object which can be rolled omnidirectionally. The manipulable object can be a captured gear-like object protruding from the mobile phone back, which can be moved, when manipulated, circularly and perpendicularly to the mobile phone back width. The manipulable objects also can be a plurality of half-dome-shaped buttons, which return to shape after being depressed. Other manipulable objects are contemplated.

In another embodiment of the mobile phone cover, the mobile phone back can be hard yet resilient in construction and configurable to attach to a mobile phone, and the mobile phone back has a plurality of manipulable objects affixed to the back. The plurality of manipulable objects are configured to provide a user with sensory feedback when at least one of the plurality of manipulable objects can be manipulated. The sensory feedback can be tactile feedback or audible feedback or a combination of the two sensory feedback modes. A first one of the plurality of manipulable objects can be a disk, which deflects when depressed, and returns to shape when released. A second one of the plurality of manipulable objects can be a ball, which performs an omnidirectional roll when manipulated, and a third one of the plurality of manipulable objects can be a disk, which rotates-in-place when manipulated, parallel to the back. Ones of the plurality of manipulable objects, when manipulated, can make a popping sound, or a muted popping sound, or a snapping sound, or a muted snapping sound, or a clicking sound or a muted clicking sound, or no sound. Other sounds are contemplated.

At least one of the plurality of manipulable objects can be a captured rocker switch-like object which rocks back and forth and makes a snapping sound or a muted snapping sound when manipulated. At least one of the plurality of manipulable objects can be a captured ball bearing-like object which can be rolled omnidirectionally without sound. Others of the plurality of manipulable objects are a plurality of captured gear-like objects protruding from the mobile phone back, each of which objects can be manipulated circularly, perpendicular to the mobile phone back width, and each of which can make a snapping or muted snapping sound, when turned.

A pliable mobile phone front can be provided. The front can be coupleable to the hard yet resilient mobile phone back. A perimeter of the pliable mobile phone front can include a raised, resilient edge. The raised, resilient edge can be formed with rectilinear edge shapes, curvilinear edge shapes, or both. The shapes may enhance shock absorption.

In yet other embodiments, a mobile phone cover, includes a mobile phone back configurable to attach to a mobile phone, a mobile phone front, coupleable to the mobile phone back, and a plurality of manipulable objects affixed to the mobile phone back, the plurality of manipulable objects configured to provide a user with sensory feedback that can be visual feedback or tactile feedback or audible feedback or a combination of two or of three sensory feedback modes, when at least one of the plurality of manipulable objects is manipulated, wherein a tactile feedback may include at least one of a depress/release, a turning-in-place, parallel with the mobile phone back, a rotation perpendicular to the mobile phone back, an omnidirectional roll in the mobile phone back, or a rocker motion on the mobile phone back, and wherein audible feedback may include at least one of a clicking sound, a popping sound, an audible snapping sound, a muted clicking sound, a muted popping sound, a muted snapping sound, or no sound. Visual feedback may include a plurality of colors disposed on the tactile feedback manipulable object, including, without limitation, black and white.

BRIEF DESCRIPTION OF THE DRAWINGS

The invention can be generally shown by way of reference to the accompanying drawings in which.

Some embodiments are described in detail with reference to the related drawings. Additional embodiments, features and/or advantages will become apparent from the ensuing description or may be learned by practicing the invention. In the figures, which are not drawn to scale, like numerals refer to like features throughout the description. The following description is not to be taken in a limiting sense, but is made merely for the purpose of describing the general principles of the invention.

DESCRIPTION OF THE EMBODIMENTS

What is provided are embodiments of a mobile phone cover, which provide simultaneous sensory-motor stimulation strategies. In particular, embodiments contemplate using the back of a mobile phone cover to provide at least one manipulable object, implementing a simultaneous sensory-motor strategy to help an individual relieve stress, increase focus, achieve calming, accomplish active listening, reduce anxiety, and minimize boredom. According to Roland Rotz and Sarah D. Wright, authors of *Fidget To Focus: Outwit Your Boredom: Sensory Strategies For Living With ADHD*: "If something we are engaged in is not interesting enough to sustain our focus, the additional sensory-motor input (from a manipulable object) that is mildly stimulating, interesting, or entertaining allows our brains to become fully engaged and allows us to sustain focus on the primary activity in which we are participating." iUniverse Books, Lincoln, Nebr. (and see http://www.fidgettofocus.com). Similar salutary effects may be experienced relative to tension, anxiety, and boredom.

Figure 1:
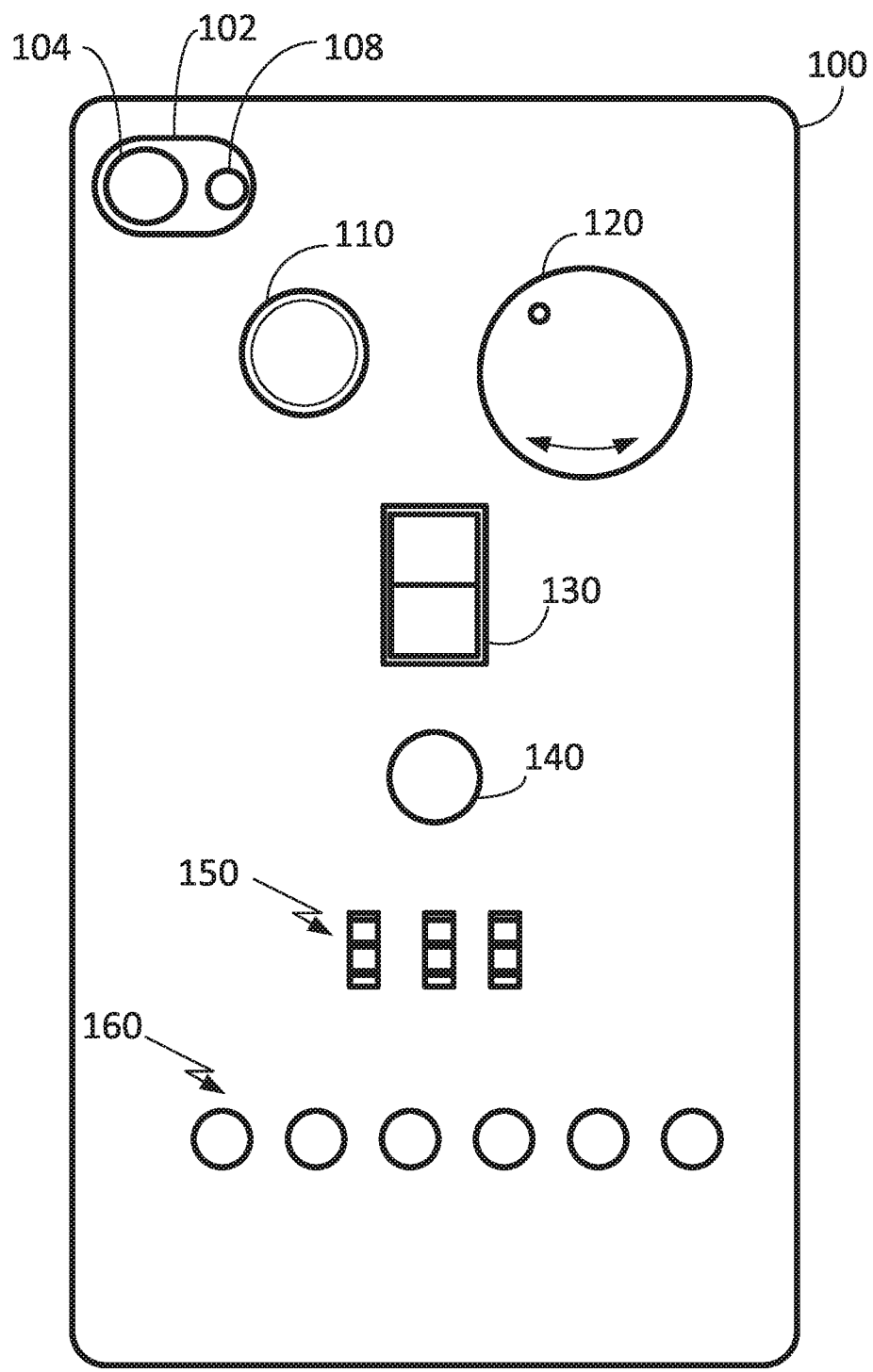
FIG. 1 is a face-on illustration of the mobile phone cover back, in accordance with the teachings of the present invention.

Accordingly, in FIG. 1, a mobile phone back 100 can be provided that includes at least one manipulable object. Mobile phone back 100 can be made of a hard yet resilient material, such as a plastic, a metal, or carbon-fiber. Mobile phone back 100 can be configurable to fit a mobile phone, with aperture 102 for a camera lens 104 and a flash light 108. Of course, various physical configurations can be produced to meet the wide array of mobile phone shapes and sizes. Although mobile phone back 100 can be provided with at least one manipulable object, it also can be provided with a plurality of manipulable objects affixed to mobile phone back 100, configured to provide a user with sensory feedback which may be, without limitation, visual, tactile, or audible, or a combination of two, or of three, sensory feedback modes, when a manipulable object is manipulated. In one embodiment, at least one of the plurality of manipulable objects makes a clicking sound, or a muted clicking sound, when manipulated. In a second embodiment, at least one of the plurality of manipulable objects makes a popping sound, or a muted popping sound, when manipulated. In a third embodiment, at least one of the plurality of manipulable objects makes a snapping sound, or a muted snapping sound, when manipulated. In a fourth embodiment, at least one of the plurality of manipulable objects makes no sound when manipulated.

In a fifth embodiment, at least one of the plurality of manipulable objects can be a press/return button 110 fitted into back 100, creating an in/out tactile sensation. In a sixth embodiment, at least one of the plurality of manipulable objects can be a captured disc 120 which turns in-place, in a circle parallel to the phone back, creating a spinning tactile sensation. In a seventh embodiment, at least one of the plurality of manipulable objects can be a captured rocker-switch-like object 130 which rocks back and forth when manipulated, creating a pushing tactile sensation. In an eighth embodiment, at least one of the plurality of manipulable objects can be a captured ball-bearing-like object 140, which can be rolled omnidirectionally when manipulated, creating a rolling tactile sensation. In a ninth embodiment, at least one of the plurality of manipulable objects can be a captured gear-like object 150 protruding from the mobile phone back, which can be moved, when manipulated, in a circle perpendicular to the mobile phone back width, creating a gear-turning tactile sensation. In a tenth embodiment, at least one of the plurality of manipulable objects can be one or more half-dome-like buttons 160, which can spring back to shape after being depressed, creating a push-and-return tactile sensation. Additional embodiments contemplated include combinations of two or more of the foregoing tactile and audible feedback sensations.

Figure 2:
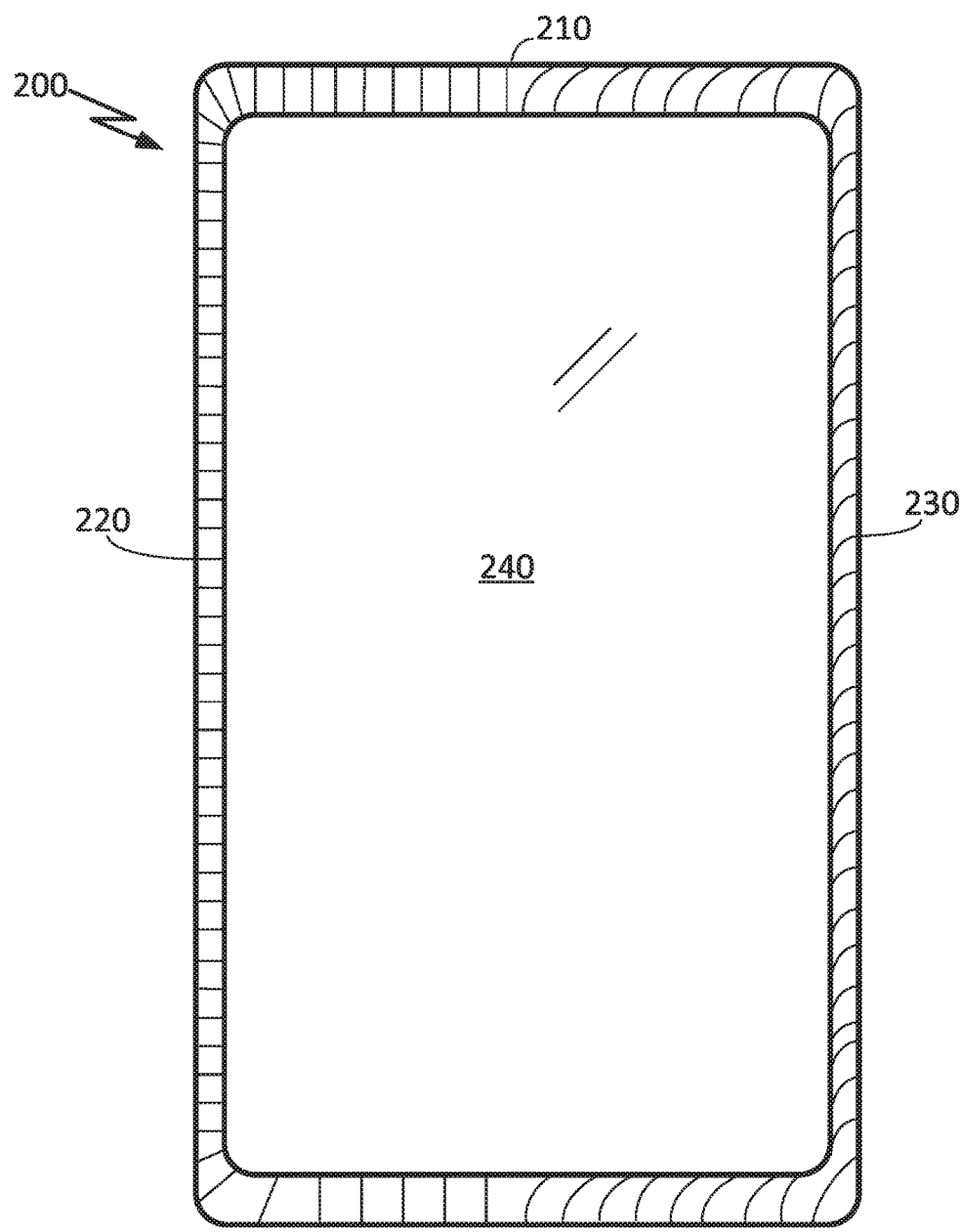
FIG. 2 is a face-on illustration of the mobile phone cover front, in accordance with the teachings of the present invention.

In yet another embodiment, FIG. 2 shows a mobile phone front 200 that can be coupleable to mobile phone back 100, with a perimeter of the mobile phone front including a raised, pliable edge 210. Raised, pliable edge 210 may be composed of, without limitation, a silicone-based material, or an elastomeric rubber-like material. The raised, pliable edge 210 may be formed with rectilinear shapes 220, curvilinear shapes 230, or both. The shapes can be included to provide additional shock-absorbance. Raised, pliable edge 210 may be formed to accept and hold in place clear plastic lens 240. In another embodiment of mobile phone front 200, pliable edge 210 may not be raised but be level with mobile phone back 100.

Although the present invention has been described by way of example with reference to the drawings, it is to be noted herein that various changes and modifications will be apparent to those skilled in the art. Therefore, unless such changes and modifications depart from the scope of the present invention, they should be construed as being included therein.

What is claimed is:
1. A mobile phone cover, comprising:
a resilient mobile phone back configurable to attach to a mobile phone;
a plurality of fidgets manipulably affixed to the resilient mobile phone back, the plurality of fidgets configured to provide a user with sensory feedback that is tactile or audible or both, when the plurality of fidgets is manipulated, a first tactile feedback includes of a depress/release button and a corresponding audible feedback is a clicking sound or a muted clicking sound, a second tactile feedback is rotary turning in place in parallel with the phone back and a corresponding audible feedback is a repetitive, rapid muted clicking sound or no sound, a third tactile feedback is a rocker motion on the mobile phone back and a corresponding audible feedback is a snapping or muted snapping sound, a fourth tactile feedback is an omnidirectional rolling in the mobile phone back and a corresponding audible feedback is no sound, a fifth tactile feedback is a plurality of gears turnable perpendicular to the phone back and the corresponding audible feedback is a snapping or a muted snapping sound, and a sixth tactile feedback is a plurality of depress/release half-domes and the corresponding audible feedback is a popping sound, with each popping sound having a different tone upon release of a corresponding one of the plurality of depress/release half-domes.

* * * * *